United States Patent
Barker et al.

(10) Patent No.: US 6,786,875 B2
(45) Date of Patent: Sep. 7, 2004

(54) MEDICAL DEVICE WITH SHIELD HAVING A RETRACTABLE NEEDLE

(75) Inventors: John M. Barker, Ventura, CA (US); Thor R. Halseth, Simi Valley, CA (US); Michael J. Botich, Oxnard, CA (US)

(73) Assignee: MDC Investement Holdings, Inc., Wilmington, DE (US)

( * ) Notice: Subject to any disclaimer, the term of this patent is extended or adjusted under 35 U.S.C. 154(b) by 0 days.

(21) Appl. No.: 09/837,539

(22) Filed: Apr. 18, 2001

(65) Prior Publication Data

US 2002/0045843 A1 Apr. 18, 2002

Related U.S. Application Data (63) Continuation-in-part of application No. 09/628,180, filed on Jul. 28, 2000, now Pat. No. 6,398,743.
(60) Provisional application No. 60/223,651, filed on Aug. 7, 2000, and provisional application No. 60/198,032, filed on Apr. 18, 2000.

(51) Int. Cl.[7] .................................................. A61B 5/00
(52) U.S. Cl. ........................ 600/585; 600/434; 600/573; 606/167; 604/164.12
(58) Field of Search ................................ 600/434, 435, 600/564, 573, 576, 581, 585; 606/167, 181; 604/110, 164.12, 171, 198

(56) References Cited

U.S. PATENT DOCUMENTS

| 4,676,249 A | 6/1987 | Arenas et al. |
| 4,787,891 A | 11/1988 | Levin et al. |
| 4,850,960 A | 7/1989 | Grayzel |
| 4,874,382 A | 10/1989 | Lindemann et al. |
| 4,886,067 A | 12/1989 | Palermo |
| 4,886,500 A | 12/1989 | Lazarus |
| 4,900,307 A | 2/1990 | Kulli |
| 4,904,242 A | 2/1990 | Kulli |
| 4,917,102 A | 4/1990 | Miller et al. |
| 4,943,283 A | * 7/1990 | Hogan ........................ 604/198 |
| 4,950,252 A | 8/1990 | Luther et al. |
| 4,955,862 A | 9/1990 | Sepetka |
| 5,046,508 A | 9/1991 | Weissler |
| 5,116,353 A | 5/1992 | Green |
| 5,163,911 A | 11/1992 | Sirimanne et al. |
| 5,217,435 A | 6/1993 | Kring |
| 5,290,244 A | 3/1994 | Moonka |
| 5,314,503 A | 5/1994 | Bobrove et al. |
| 5,318,585 A | 6/1994 | Guy et al. |
| 5,330,432 A | 7/1994 | Yoon |
| 5,336,441 A | 8/1994 | Shah et al. |
| 5,360,410 A | 11/1994 | Wacks |
| 5,376,075 A | * 12/1994 | Haughton et al. .......... 604/158 |
| 5,395,337 A | 3/1995 | Clemens et al. |
| 5,425,718 A | 6/1995 | Tay et al. |
| 5,531,692 A | 7/1996 | Rogers |
| 5,578,053 A | * 11/1996 | Yoon .......................... 606/185 |
| 5,685,862 A | 11/1997 | Mahurkar |

(List continued on next page.)

FOREIGN PATENT DOCUMENTS

| GB | 2248021 A | * 3/1992 | |
| WO | WO 200020058 A1 | * 4/2000 | A61M/5/178 |

OTHER PUBLICATIONS

U.S. application No. 09/628,180 filed on Jul. 28, 2000.

Primary Examiner—Charles Marmor
(74) Attorney, Agent, or Firm—Stephen H. Eland; Dann, Dorfman, Herrell and Skillman (57) ABSTRACT

Needle-bearing medical devices are provided for fluid infusion, fluid transfusion, and inserting a guide wire. After use the needle is shielded to render the contaminated needle safe to prevent inadvertent needle sticks. The device includes a housing and a needle having a sharpened tip. A biasing element biases the needle toward a position in which the sharpened tip is shielded.

10 Claims, 9 Drawing Sheets

U.S. PATENT DOCUMENTS

| | | |
|---|---|---|
| 5,695,475 A | 12/1997 | Best, Jr. et al. |
| 5,695,479 A | 12/1997 | Jagpal |
| 5,702,367 A | 12/1997 | Cover et al. |
| 5,735,813 A | 4/1998 | Lewis |
| 5,749,371 A | 5/1998 | Zadini et al. |
| 5,749,857 A | 5/1998 | Cuppy |
| 5,788,654 A | 8/1998 | Schwager |
| 5,846,226 A | 12/1998 | Urmey |
| 5,851,196 A * | 12/1998 | Arnett ..................... 604/110 |
| 5,871,470 A | 2/1999 | McWha |
| 5,882,342 A | 3/1999 | Cooper et al. |
| 5,919,172 A | 7/1999 | Golba, Jr. |
| 5,935,108 A | 8/1999 | Katoh et al. |
| 5,989,220 A | 11/1999 | Shaw et al. |
| 6,050,976 A | 4/2000 | Thorne et al. |
| 6,077,244 A * | 6/2000 | Botich et al. ............... 604/110 |
| 6,080,138 A * | 6/2000 | Lemke et al. ............... 128/919 |
| 6,099,504 A | 8/2000 | Gross et al. |
| 6,162,195 A | 12/2000 | Igo et al. |
| 6,398,743 B1 * | 6/2002 | Halseth et al. ............. 600/585 |

* cited by examiner

MEDICAL DEVICE WITH SHIELD HAVING A RETRACTABLE NEEDLE

RELATED APPLICATIONS

This application is a continuation-in-part of U.S. application Ser. No. 09/628,180, filed Jul. 28, 2000, now U.S. Pat. No. 6,398,743. This application also claims priority to U.S. Provisional Application No. 60/198,032, filed Apr. 18, 2000 and U.S. Provisional Application No. 60/223,651 filed Aug. 7, 2000. Each of the foregoing applications is hereby incorporated herein by reference.

FIELD OF INVENTION

The present invention relates to medical devices for fluid infusion, fluid transfusion, and inserting a guide wire into a patient. In a particular, the present invention relates to medical devices having a sharpened needle used for introducing a guide wire into a patient. The needle pierces the patient to provide vascular access, and the guide wire is then inserted into the patient through the needle. After use, the sharpened needle is protected against inadvertent contact. More specifically, after use, the needle is retracted so that the sharpened tip of the needle is enclosed within the device.

BACKGROUND

Various types of medical devices employ a needle for piercing the skin of a patient for diagnostic or therapeutic purposes. One such device is an Epidural needle for introducing medicine to a patient during an Epidural procedure. Another such device is a device for infusing or withdrawing blood or plasma in a patient. Yet another such device is a device for introducing a guidewire into a patient. The guidewire is then used to guide a separate element such as an enlarged bore introducer sheath and dilator into the patient. Once the guidewire is properly positioned, the insertion device is withdrawn leaving the guidewire in place in the blood vessel. Handling of such medical devices after the needle is withdrawn from the patient can result in transmission of various pathogens, most notably human immune virus (HIV), due to in inadvertent needle stick to medical personnel.

SUMMARY OF THE INVENTION

In light of the foregoing, the present invention provides a method and apparatus for inserting a needle into a patient and rendering the device safe after use to prevent inadvertent contact with the contaminated needle. The present invention also provides a method and apparatus for inserting a guide wire into a patient and rendering the device safe after use to prevent inadvertent contact with the contaminated needle.

In accordance with one aspect of the invention, a medical device is provided that has a needle having a sharpened tip projecting forwardly from a housing. Prior to use a shield sheaths a portion of the needle so that the sharpened tip projects forwardly from the sheath. After use the sharpened tip is retracted into the shield. A biasing element biases the needle toward the retracted position.

In accordance with another aspect of the invention, a medical device is provided that has a needle having a sharpened tip projecting forwardly from a housing. Prior to use a shield sheaths a portion of the needle so that the sharpened tip projects forwardly from the sheath. After use the sharpened tip is retracted into the shield. A biasing element biases the needle toward the retracted position, and a hub connected with the needle includes a guide for guiding a guide wire into the patient through the needle and a connector for attaching a fluid reservoir to the device.

The present invention also provides a medical device having a needle having a sharpened tip projecting forwardly from a housing. After use, the sharpened tip of the needle is shielded against inadvertent contact. A biasing element is operable to displace the sharpened tip of the needle into the shielded position. The device includes a connector for attaching a fluid collection device to the housing. The connector also includes a first port, and the device includes a second port in fluid communication with the needle. An adapter associated with the second port is configured for receiving and guiding a guide wire through the second port and into the needle.

The present invention also provides a method for inserting a guide wire into a patient using a needle-bearing medical device having first and second ports. According to the method, a needle is inserted into a patient and blood is aspirated through the first port. The needle is retracted so that the sharpened tip of the needle is shielded to protect against inadvertent contact. A guide wire is then inserted into the patient through the second port.

The present invention also provides a method for inserting a guide wire into a patient using a needle-bearing medical device having a port. The needle is inserted into the patient and a fluid reservoir is attached to the port for collecting blood from the patient. The fluid collection device is detached from the port and a guide wire is inserted into the patient through the device. The needle is retracted to shield the needle to prevent inadvertent contact with the contaminated needle.

Accordingly, when configured and used as described above, the present invention provides a safe and effective method for infusing medicine, transfusing blood or plasma, or inserting a guide wire into a patient. In addition, the device is designed to improve manufacturing efficiencies thereby reducing the overall cost of the device.

DESCRIPTION OF THE DRAWINGS

The foregoing summary as well as the following description will be better understood when read in conjunction with the figures in which.

DETAILED DESCRIPTION OF THE PREFERRED EMBODIMENT

Figure 1:
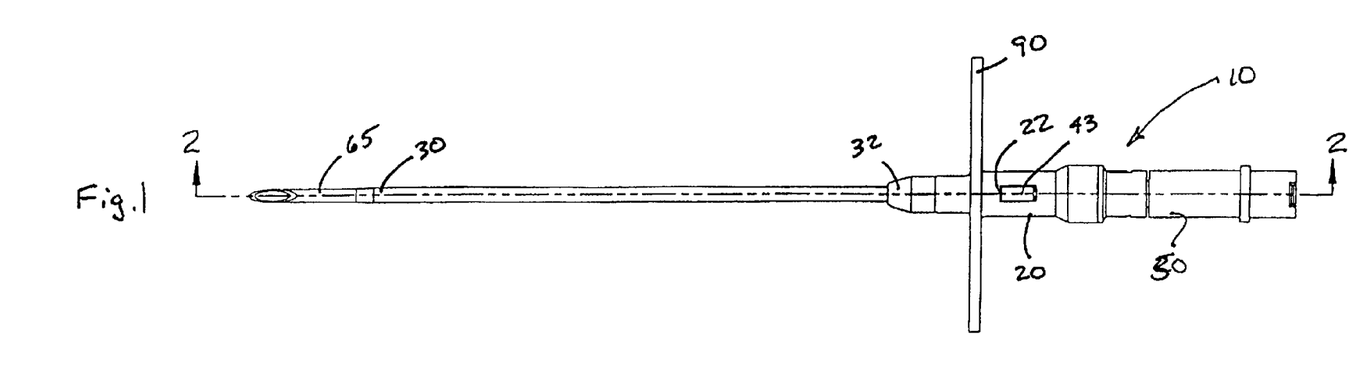
FIG. 1 is a plan view of a medical device for fluid transfusion having a retractable needle.

Referring now to the figures in general and to FIG. 1 specifically, a medical device for fluid infusion is designated generally 10. The device 10 includes a sharpened needle 65 for inserting the device into a patient. After the needle is inserted into the patient, fluid can be infused into the patient through the needle. After use, the needle 65 is retracted into the device 10 so that the sharpened tip of the needle is enclosed, thereby preventing inadvertent contact with the contaminated needle.

Figure 2:
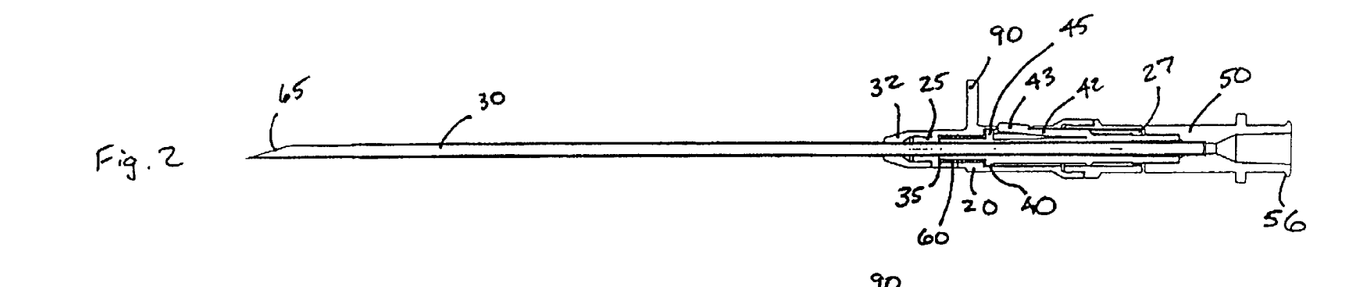
FIG. 2 is a cross-sectional view of the medical device illustrated in FIG. 1 taken along line 2—2.

Referring now to FIGS. 1 and 2, the device includes an elongated hollow barrel 20. The needle 65 projects forwardly from the barrel, with a sheath 30 surrounding the length of the needle. The needle 65 is attached to a needle hub 40 disposed within the barrel 20. A spring 60 disposed within the barrel biases the needle hub 40 and the attached needle 65 rearwardly toward a retracted position. A needle retainer 42 releasably retains the needle hub against the bias of the spring 60. A connector hub 50 at the rearward end of the device 10 allows a fluid source to be attached to the device for infusing fluid, such as medicinal fluid, through the needle and into the patient.

The medical professional using the device 10 can retract the needle by pressing a button 43, which disengages the needle retainer 42. The spring 60 then propels the needle 65 rearwardly so that the sharpened tip of the needle is enclosed within the shield 30. In this way, the contaminated needle 65 is protected against inadvertent contact.

The details of the device will now be explained in greater detail. As shown in FIG. 2, the barrel is a generally cylindrical barrel having a hollow central bore. A locking aperture 22 in the sidewall of the barrel 20 is configured to cooperate with the needle retainer 42 as described further below. The rearward end of the barrel is generally open for receiving the needle hub 40. The forward end of the barrel 20 is generally closed, having a reduced diameter opening through which the needle 65 extends. Optionally, a seal 35, such as an O-ring may be provided to form a fluid seal between the reduced diameter opening and the needle 65 to prevent fluid from leaking from the shield 30 into the barrel 20 after retraction.

Although the barrel 20 may be formed as a single piece, in the present instance, the barrel is formed in two portions that are snap-fit together. Alternatively, the two portions can be connected by ultrasonic welding or adhesive. In addition, the barrel may include a pair of opposing axial slots formed in the interior surface of the barrel, adjacent the rearward end of the barrel. Such slots form a guide track that cooperates with the needle hub 40 to guide the needle 60 during retraction. Additionally, the slots prevent the button 43 from being twisted relative to the locking aperture 22 when a fluid collection device is attached to the device 10.

The barrel 20 further includes a flange 27 projecting radially inwardly from the interior surface of the barrel, adjacent the rearward end of the barrel. The flange 27 forms a stop that cooperates with the needle hub 40 to limit rearward displacement of the needle hub, which in turn limits the retraction of the needle.

Preferably, a push bar or wing 90 is attached to the housing 20. The push bar 90 is a generally planar surface disposed substantially normal to the axis of the housing. In this way, insertion force can be applied to the push bar 90 to aid in inserting the device 10 into the patient.

Referring again to FIGS. 1 and 2, the details of the needle hub 40 are illustrated. The needle hub 40 is generally cylindrical having an internal bore for receiving the needle 65. Preferably, the needle retainer 42 is integrally formed with the needle hub 40. The needle retainer includes an axially elongated radially deformable arm with a latch or button 43. The button 43 is configured to cooperate with the locking aperture 22 in the barrel, to releasably engage the needle hub 40 with the barrel 20. The forward end of the needle hub 40 flares outwardly forming a circumferential flange 45 having an external diameter corresponding to the central bore of the barrel. In this way, as the needle hub 40 is displaced rearwardly during retraction, the flange 45 slides along the interior bore to guide the needle hub.

Figure 3:
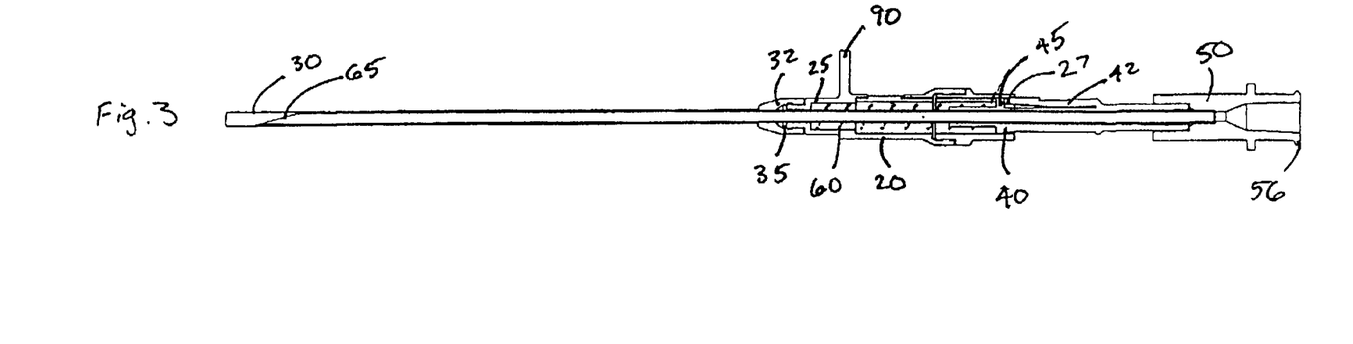
FIG. 3 is a cross-sectional view of the medical device illustrated in FIG. 2, illustrating the device in a retracted position.

The needle 65 is operable between a projecting position illustrated in FIG. 2 and a retracted position illustrated in FIG. 3. In the projecting position, the needle projects forwardly from the barrel so that the sharpened tip of the needle is exposed to pierce the patient and guide the shield 30 into the patient. In the retracted position, the sharpened tip of the needle is disposed within the shield 30 to prevent inadvertent contact with the contaminated needle. The spring 60 biases the needle 65 rearwardly toward the retracted position. The needle retainer 42 releasably retains the needle 65 in the projecting position against the bias of the spring 60.

The needle 65 extends through the central bore of the needle hub 40, and through the opening in the barrel tip 25 so that the sharpened tip of the needle projects forwardly from the barrel. The shield 30 is fixedly attached to the barrel tip 25 so that the shield also projects forwardly from the barrel 20. More specifically, a shield connector 32 is configured to cooperate with the barrel tip 25 to fixedly attach the shield to the barrel. The shield connector 32 includes an internal cavity configured to form a snap fit with the barrel tip 25. The shield 30 is fixedly attached to the shield connector 32, such as by adhesive or welding. In this way, the shield 30 is fixedly attached to the barrel 20 when the shield connector 32 is snapped onto the barrel tip 25.

The shield 30 is in the form of a relatively thin-walled cannula, overlying the needle 65 in telescoping relation. Specifically, the interior diameter of the shield is substantially the same as the external diameter of the needle 65. Preferably, the interior diameter of the shield 30 is the same as or several thousandths of an inch larger than the external diameter of the needle so that the needle 65 can readily slide within the shield.

As shown in FIG. 3, the forward end of the shield 30 tapers inwardly forming a thin wall with a feather edge, which provides a smooth transition between the forward end of the shield 30 and the needle 65. In this way, when the needle 65 is inserted into the patient, the overlying shield 30 is also readily inserted into the patient.

A stop limits the rearward travel of the needle hub 40 to limit the distance that the needle 65 is retracted. Specifically, the forward end of the needle hub flares outwardly forming an enlarged head 45. The enlarged head 45 engages the flange 27 on the interior of the barrel 20 when the needle is retracted. In this way, the engagement between the flange 27 and the enlarged head 45 limits the rearward displacement of the needle 65.

Preferably, prior to retraction, the axial distance between the flange 27 and the enlarged head 45 is less than the length of the shield 30 that projects forwardly from the barrel 20. More specifically, preferably the axial distance is less than half the length of the shield that projects forwardly from the barrel 20. It is further preferable that the axial distance be substantially less than one quarter the length of the shield that projects from the barrel. In this way, after retraction, the sharpened tip of the needle is enclosed within the shield 30, rather than being retracted into the barrel 20.

The device 10 further includes elements for impeding re-extension of the needle 65 after retraction, so that the contaminated sharpened tip of the needle is not exposed. Specifically, a pair of opposing radially deformable latches are integrally formed in the side of the barrel 20. A pair of cooperating notches are formed in the needle hub 40. When the needle hub 40 retracts rearwardly, the needle hub deforms the latches radially outwardly so that the needle hub is displaced between the latches. When the needle hub is displaced rearwardly so that the notches on the needle hub are aligned with the latches, the latches, which are biased radially inwardly, are displaced inwardly into engagement with the notches, retaining the needle hub and needle against forward displacement. In this way, the latches and notches prevent the needle from being re-extended from the shield after retraction.

A connector hub 50 attached to the needle hub 40 provides an access port for attaching a fluid reservoir to the device for infusing fluid into the patient. The connector hub 50 includes a central bore in fluid communication with the needle 65. In the present instance, the rearward end of the needle 65 is connected with the connector hub 50.

The connector hub 50 has an open rearward end and preferably forms a connector in the form of a Luer fitting for attaching a medical device, such as a fluid reservoir as discussed further below. In addition, preferably a lock 56 is formed on the rearward end of the connector hub for locking the separate device to the connector hub. More specifically, preferably, the lock 56 is a threaded Luer lock formed on the exterior of the connector hub.

In the present instance, the needle hub 40 and connector hub 50 have been described as two separate elements connected together. However, the two elements can alternatively be formed as a single element.

Retracting the needle into the shield rather than the barrel has several benefits. For instance, the overall length of the barrel can be reduced because the barrel need not be long enough to accommodate the retracted needle.

After use, the shield 30 shields the sharpened tip of the needle 65 against inadvertent contact. Preferably, the shield 30 is somewhat flexible. In addition, the shield is preferably formed with sufficient column strength to prevent the shield 30 from collapsing axially in response to an axial force after retraction. This columnar strength prevents the shield from readily buckling axially after retraction, which could expose the contaminated needle. In other words, the shield 30 is preferably laterally flexible, but is substantially axially incompressible. In addition, preferably the shield is substantially puncture resistant, so that the needle will not puncture the shield if the shield buckles or compress. In this way, the shield protects the contaminated needle after retraction. In the present instance the shield is formed of Teflon. However, a variety of other known plastic materials may be used to form the shield.

Configured in this way, the device 10 is preferably used to infuse fluid into a patient as follows. The needle 65 and shield pierce the skin of a patient and the needle is advanced to the proper location within the patient. In certain instances, additional insertion force may be applied by pressing forwardly on the push bar 90. This is particularly helpful in situations in which the forward tip of the needle need not be sharp and/or the needle must be inserted through tough material, such as in needles used for blunt dissection. For instance, when inserting an Epidural needle, the needle is relatively dull and is inserted adjacent the spinal cord, without piercing the spinal cord. In such instances additional force must be applied to insert the needle to the proper location to apply anesthesia. Once the needle is in place within the patient, the needle is retracted into the shield, to cover the needle while the shield is within the patient. If desired, a catheter may be inserted into the patient through the needle and shield. A fluid source can then be attached to the catheter to deliver medicinal fluid to the patient. Alternatively, the fluid source may be attached to the connector hub 50 and medicinal fluid may be delivered to the patient through the needle and shield. After use, the device 10 is withdrawn from the patient. Since the needle is shielded, the used device may be discarded without risk of inadvertent contact with the contaminated needle.

Figure 4:
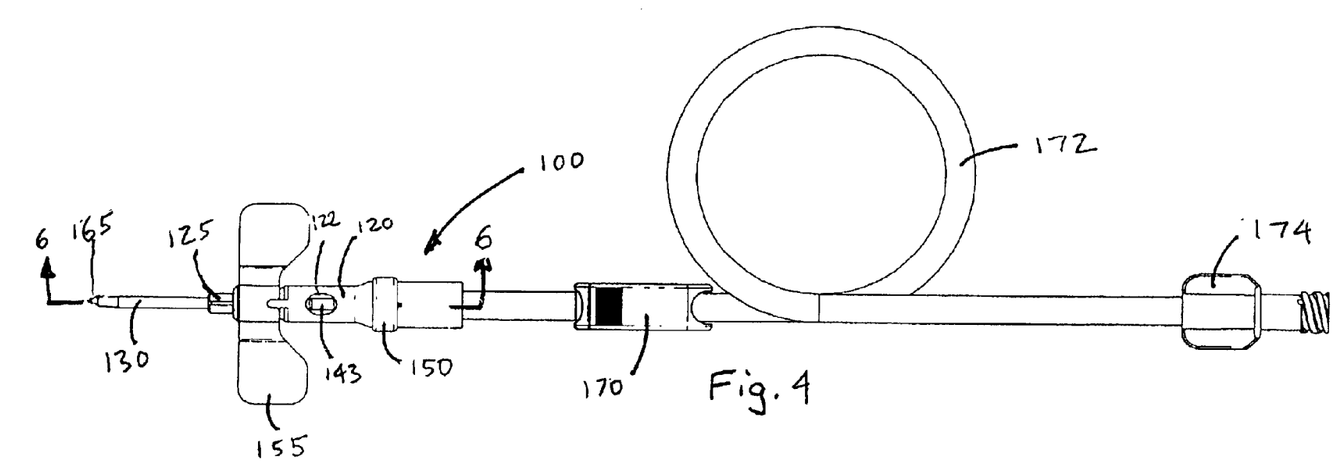
FIG. 4 is a plan view of a medical device for fluid transfusion having a retractable needle.

Referring now to FIG. 4 specifically, a medical device for fluid transfusion is designated generally 100. As discussed further below, preferably the device is particularly suited for use in connection with hemodialysis, which utilizes a pair of the devices. Specifically, one is inserted into the patient to withdraw blood, which is fed to a hemodialysis machine. The second device 100 is inserted into the patient to return the blood from the dialysis machine. In other words, blood flows from the patient through one of the devices, into the hemodialysis machine, and then returns through the second device while the patient is hooked up to the hemodialysis machine.

The device 100 includes a sharpened needle 65 for inserting the device intravascularly. The needle 165 is in fluid communication with tubing 172, which in turn is connected with a dialysis machine or fluid reservoir. After the needle is inserted into the patient, fluid can either be withdrawn from the patient through the needle and collected in a reservoir or container attached to the tubing 172, or fluid can be infused into the patient through the needle. After use, the needle 165 is retracted into the device 100 so that the sharpened tip of the needle is enclosed, thereby preventing inadvertent contact with the contaminated needle.

Figure 6:
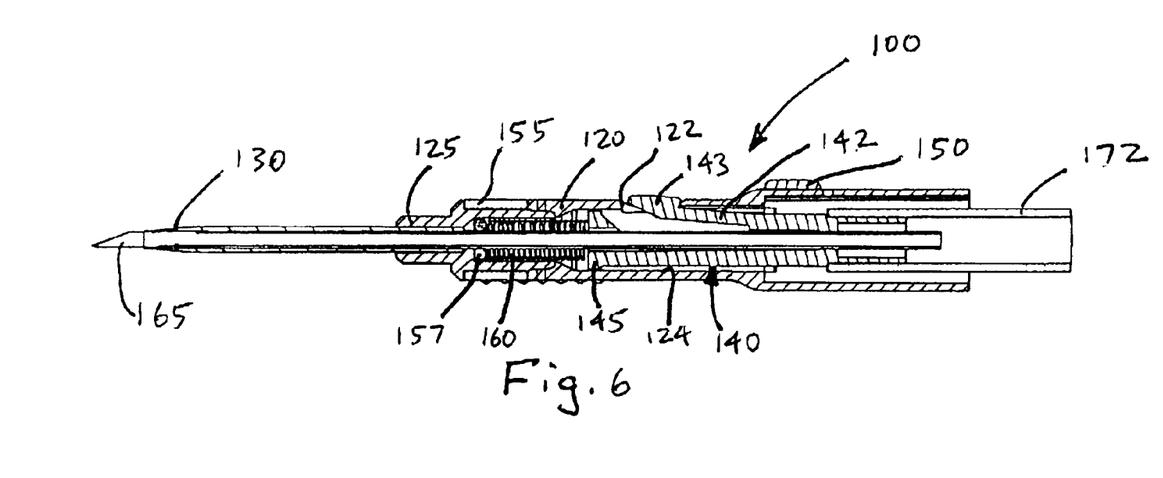
FIG. 6 is a cross-sectional view of the medical device illustrated in FIG. 4, taken along line 6—6.
Figure 7:
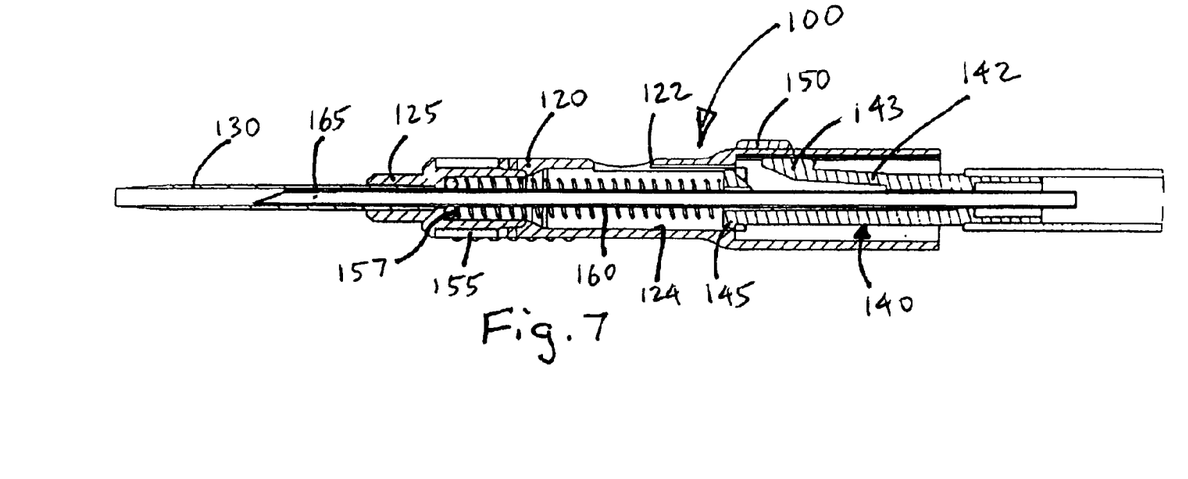
FIG. 7 is a cross-sectional view of the medical device illustrated in FIG. 6, illustrating the device in a retracted position.

Referring now to FIGS. 6 and 7, the device includes an elongated hollow housing 120. The needle 165 projects forwardly from the housing, with a sheath 130 surrounding the length of the needle. The needle 165 is attached to a needle hub 140 disposed within the housing 120. A spring 160 disposed within the housing biases the needle hub 140 and the attached needle 165 rearwardly toward a retracted position. A needle retainer 142 releasably retains the needle hub against the bias of the spring 160. The tubing 172 is attached to the rearward end of the needle hub 140 so that the needle 165 is in fluid communication with the tubing. A Luer fitting 174 at the rearward end of the tubing 172 allows the tubing to be readily connected with a dialysis machine or a fluid reservoir. In addition, a clamp 170 attached to the tubing 172 allows the medical professional to control the transfusion of fluid by selectively pinching the tubing with the clamp 174.

After insertion, the medical professional using the device 100 presses a button 43, which disengages the needle retainer 142, and the spring 160 propels the needle 165 rearwardly so that the sharpened tip of the needle is enclosed within the shield 130. In this way, the needle 165 is shielded to prevent the needle from inadvertently damaging the patient during use and to prevent inadvertent contact with the contaminated needle after use.

Figure 5:
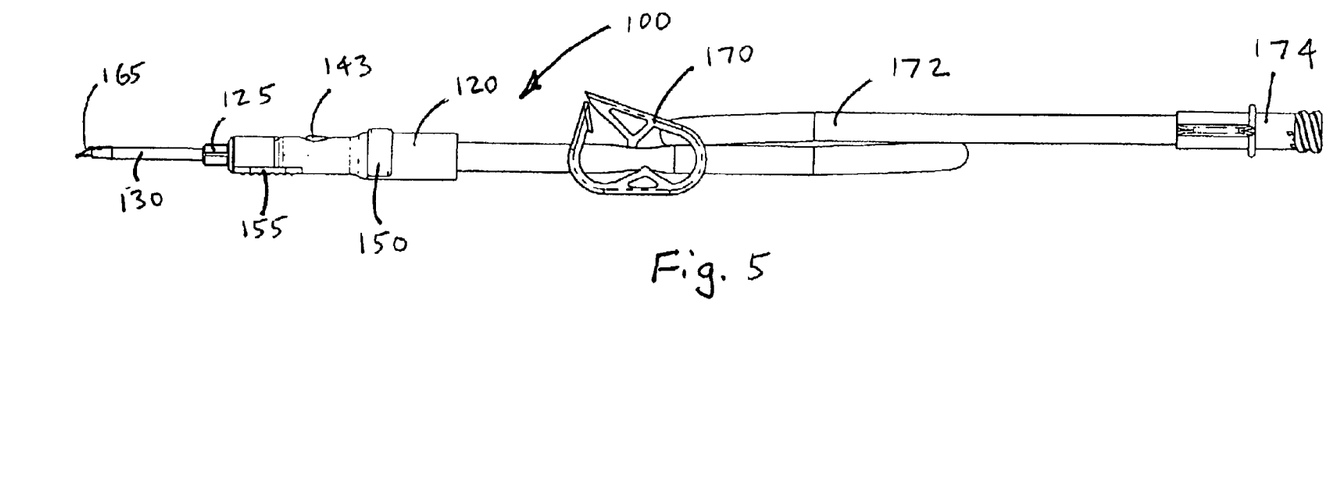
FIG. 5 is a side elevational view of the medical device illustrated in FIG. 4.
Figures 8, 9:
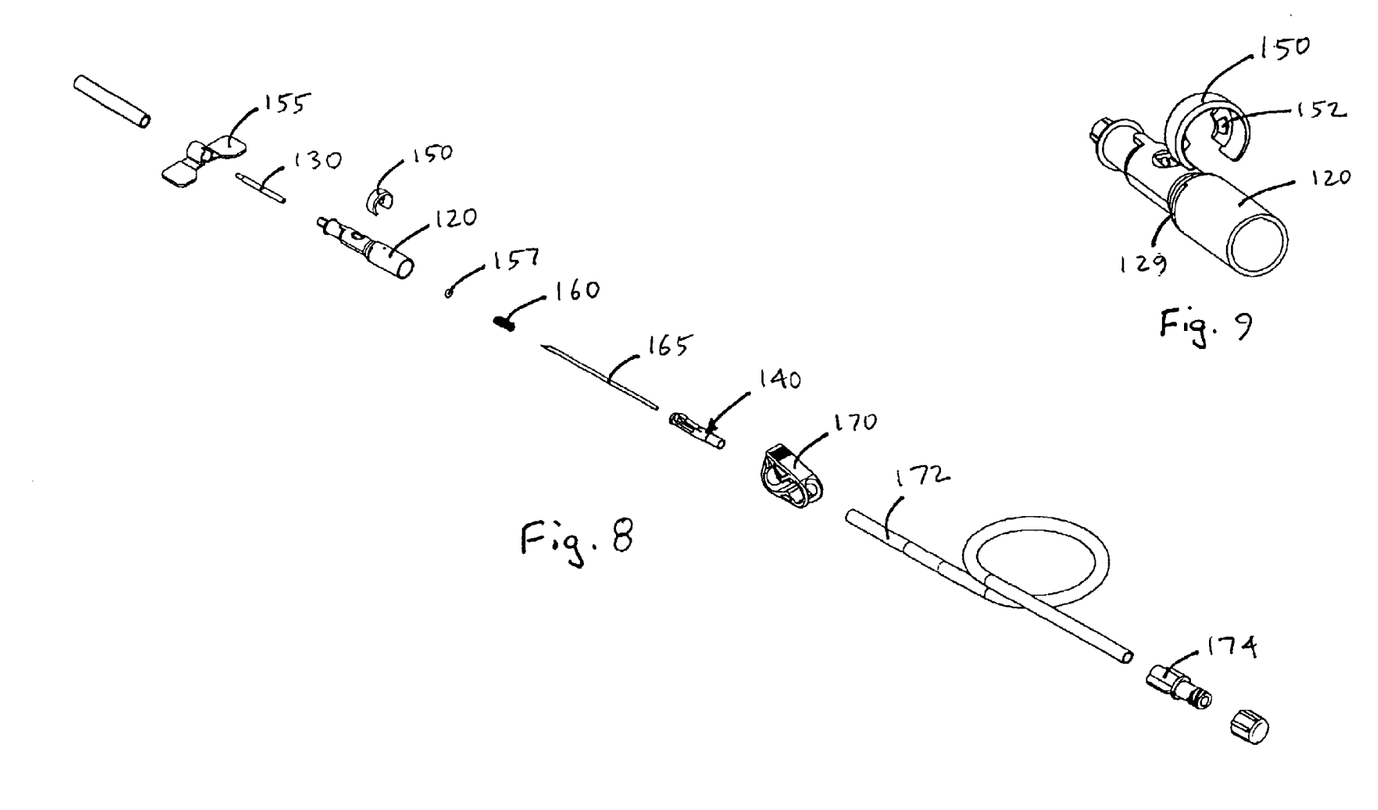
FIG. 8 is an exploded perspective view of the medical device illustrated in FIG. 4.
FIG. 9 is an enlarged fragmentary exploded perspective view of the barrel of the medical device illustrated in FIG. 4.

As shown in FIGS. 4–6, the housing is a generally cylindrical barrel having a hollow central bore 124. A locking aperture 122 in the sidewall of the housing 120 is configured to cooperate with the needle retainer 142 as described further below. The rearward end of the housing flares outwardly having a larger diameter than the forward portion of the housing. The rearward end of the housing is generally open for receiving the needle hub 140 and the tubing 172. The forward end of the housing 120 is open. A separate tip 125 fixedly attached to the forward end of the housing forms a reduced diameter opening at the forward end of the housing through which the needle 165 extends. As shown in FIG. 9, the barrel includes a pair of opposing circumferential slots for receiving a locking clip 150 as will be discussed further below.

A pair of wings 155 are attached to the housing 120. The wings 155 are attached to a central hub that circumscribes the housing 120. A relief line located between each wing and the central hub forms a living hinges so that the wings can be folded up during the insertion procedure. After insertion, the wings 155 are folded flat against the skin of the patient and taped to the patient to retain the device on the patient during fluid transfusion.

Referring again to FIGS. 6 and 7, the details of the needle hub 140 are illustrated. The needle hub 140 is generally cylindrical having an internal bore for receiving the needle 165. Preferably, the needle retainer 142 is integrally formed with the needle hub 140. The needle retainer includes an axially elongated radially deformable arm with a latch or button 143. The button 143 is configured to cooperate with the locking aperture 122 in the housing, to releasably engage the needle hub 140 with the housing 120. The forward end of the needle hub 140 flares outwardly forming a circumferential flange 145 having an external diameter corresponding to the central bore 124 of the housing. In this way, as the needle hub 140 is displaced rearwardly during retraction, the flange 145 slides along the interior bore 124 to guide the needle hub.

The needle 165 is operable between a projecting position illustrated in FIG. 6 and a retracted position illustrated in FIG. 7. In the projecting position, the needle projects forwardly from the housing so that the sharpened tip of the needle is exposed to pierce the patient and guide the shield 130 into the patient. In the retracted position, the sharpened tip of the needle is disposed within the shield 130 to prevent inadvertent contact with the contaminated needle. The spring 160 biases the needle 165 rearwardly toward the retracted position. The needle retainer 142 releasably retains the needle 165 in the projecting position against the bias of the spring 160.

The needle 165 extends through the central bore of the needle hub 140, and through the opening in the housing tip 125 so that the sharpened tip of the needle projects forwardly from the housing. The shield 130 is fixedly attached to the housing tip 125 so that the shield also projects forwardly from the housing 120. The shield 130 is in the form of a relatively thin-walled cannula, overlying the needle 165 in telescoping relation. The forward end of the shield 130 tapers inwardly forming a knife edge which provides a smooth transition between the forward end of the shield 130 and the needle 165. In this way, when the needle 165 is inserted into the patient, the overlying shield 130 is also readily inserted into the patient.

A stop limits the rearward travel of the needle hub 140 to limit the distance that the needle 165 is retracted. Specifically, as shown in FIG. 9, a horseshoe-shaped locking clip 150 circumscribes the housing 120. The locking clip 150 includes a pair of locking tabs 152 projecting radially inwardly. When the locking clip 150 is attached to the housing the locking tabs 152 project radially inwardly through the slots 129 in the side of the housing. The locking tabs 152 engage the flange 145 on the needle hub 140 when the needle is retracted. In this way, the engagement between the locking tabs 152 and the flange 145 limit the rearward displacement of the needle 165.

Preferably, prior to retraction, the axial distance between the locking tabs 152 and the flange 145 is less than the length of the shield that projects forwardly from the housing 120. More specifically, preferably the axial distance is less than half the length of the shield that projects forwardly from the housing 120. In this way, after retraction the sharpened tip of the needle is enclosed within the shield 130, rather than being retracted into the housing 120.

Retracting the needle into the shield rather than the housing has several benefits. The overall length of the housing can be reduced because the housing need not be long enough to accommodate the retracted needle. In addition, the needle 165 provides support for the shield 130 to prevent the shield frown collapsing or buckling radially inwardly in response to external forces. For instance, in one application the device 100 is used in conjunction with an elastomeric shunt having a pierceable wall. The shunt joins one of the patient's vein's with one of the patient's arteries. The shunt is formed of an elastomeric material, and the device 100 is inserted into the shunt by piercing the sidewall of the shunt and advancing the device into the shunt so that the needle and shield are in fluid communication with the patient's vein and/or artery. While the device 100 is inserted into the shunt, the medical professional actuates retraction by depressing the button 143. The needle retainer 142 is thereby displaced radially inwardly out of engagement with the housing, and the spring 160 displaces the needle 165 rearwardly into the retracted position. As shown in FIG. 7, the needle remains within the shield 130 after retraction. Since the shield 130 is still disposed within the shunt after retraction, the sidewall of the elastomeric shunt will tend to press radially inwardly against the walls of the shield. The rigidity of the needle prevents the sidewall of the shunt frown collapsing the shield, which would cut off fluid transfusion through the device.

After use, the shield 130 shields the sharpened tip of the needle 165 against inadvertent contact. Preferably, the shield 130 is somewhat flexible so that the device 100 is more comfortable for the patient 128 while it is inserted in the patient. In addition, the shield is formed with sufficient columns strength to prevent the shield 130 frown collapsing axially in response to an axial force after retraction. This columnar strength prevents the shield frown readily buckling axially after retraction, which could expose the contaminated needle.

Referring to FIGS. 6 and 8, the device is assembled as follows. The wings 155 are attached to the housing 120 and the seal 157 and sprint 160 are inserted into the housing through the rearward open end of the housing. The needle hub 140 is inserted into the central bore 124 of the housing so that needle hub bears against the spring and the button 143 engages the locking aperture 122. The seal provides a fluid-tight seal to prevent fluid from leaking into the housing between the shield and the needle. After the needle hub is inserted into the housing, the locking clip 150 is snapped onto the housing. The needle is then inserted through the forward end of the housing until the rearward end of the needle is disposed within the needle hub 140. After the needle is located within the needle hub, the needle is bonded to the needle hub. The tip 125 and attached shield 130 are then attached to the forward end of the housing to capture the spring between the tip and the needle hub.

In the embodiment illustrated in FIGS. 4–9, the device is described as using a one-piece housing. It may be desirable to provide a two-piece barrel so that the needle, and needle are exposed after assembly. Such a structure is disclosed in FIGS. 10–11, in which elements similar to the elements in the first embodiment are designated with like reference numbers with the addition of 200s.

Figure 10:
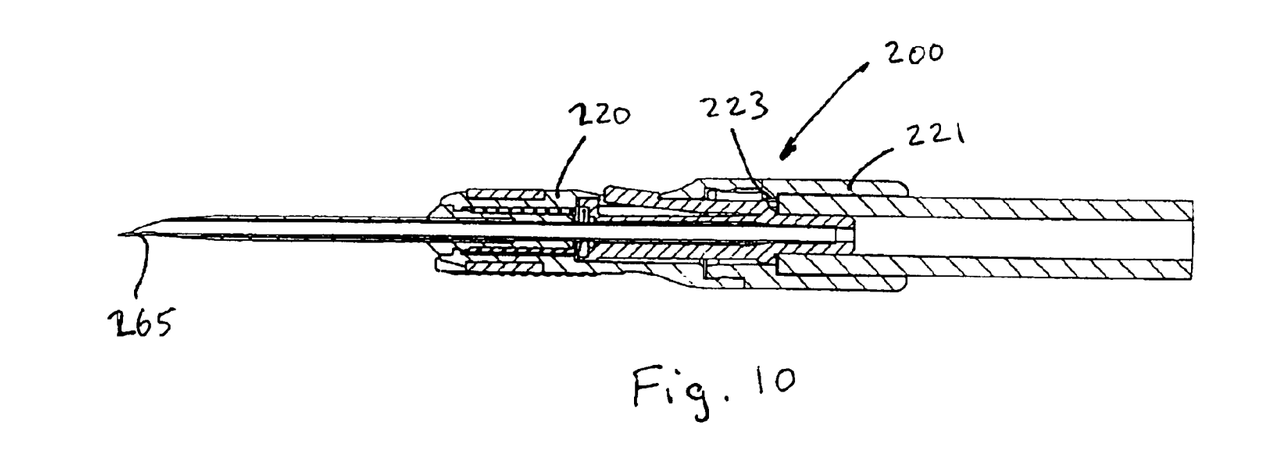
FIG. 10 is a cross-sectional view of an alternative embodiment of a medical device for fluid transfusion having a retractable needle.
Figure 11:
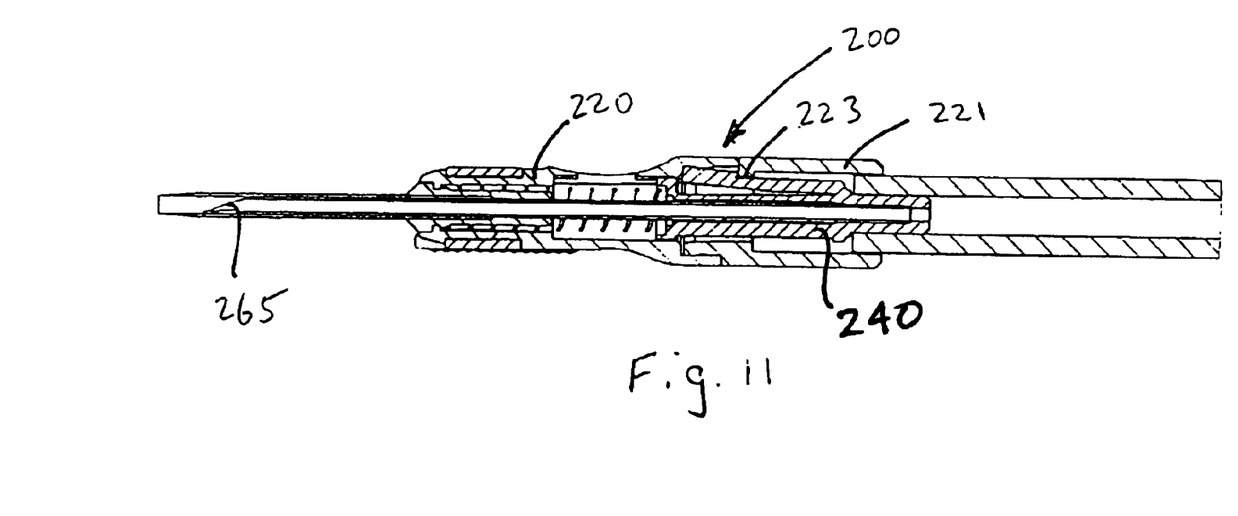
FIG. 11 is a cross-sectional view of the device illustrated in FIG. 10, illustrating the device in a retracted position.

Referring to FIGS. 10–11, the device 200 includes a forward housing 220 and a rearward housing 221. During assembly, the needle hub 240 is inserted into the forward housing 220. The rearward end of the needle hub 240 projects rearwardly from the forward housing 220. Since the needle hub 240 and needle 265 are exposed, adhesive can be readily applied to bond the needle to the needle hub. The rearward housing 221 is then attached to the forward housing 220 to enclose the needle hub 240. The rearward housing 221 includes a flange 223 that cooperates with the needle retainer to limit the rearward retraction of the needle 265.

Figure 12:
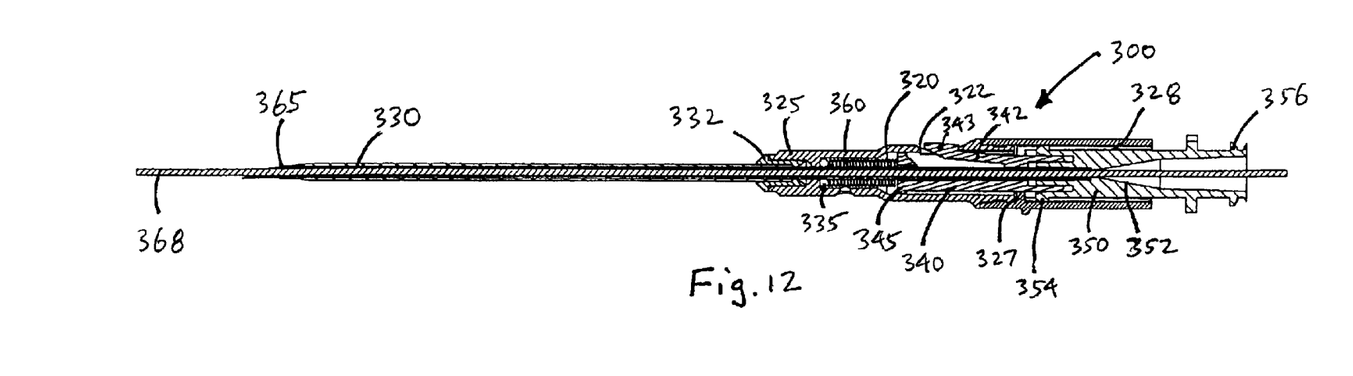
FIG. 12 is a cross-sectional view of a medical device having a retractable needle for inserting a guide wire.

In another embodiment of the present invention, referring now to FIG. 12 specifically, a medical device for inserting a guide wire is designated generally 300. The device 300 includes a sharpened needle 365 for inserting the device vascularly. After the needle is inserted into the patient the needle may be retracted into the device 300 so that the sharpened tip of the needle is enclosed. A guide wire can then be inserted into the patient through the needle. After use, the device 300 is withdrawn with the needle safely shielded.

Figure 13:
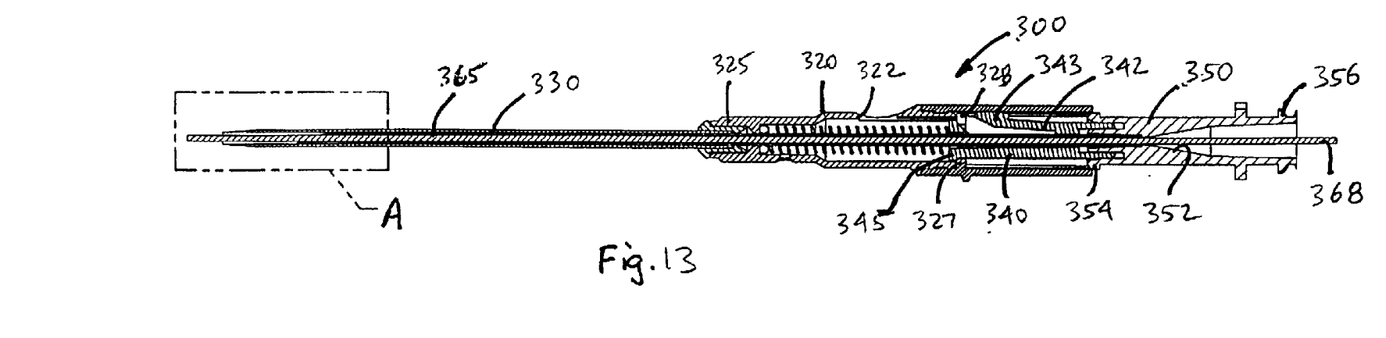
FIG. 13 is a cross-sectional view of the medical device illustrated in FIG. 12, illustrating the needle in a retracted position.

Referring now to FIGS. 12 and 13, the device includes an elongated hollow barrel 320. The needle 365 projects forwardly from the barrel, with a sheath 330 surrounding the length of the needle. The needle 365 is attached to a needle hub 340 disposed within the barrel 320. A spring 360 disposed within the barrel biases the needle hub 340 and the attached needle 365 rearwardly toward a retracted position. A needle retainer 342 releasably retains the needle hub against the bias of the spring 360. A port at the rearward end of the device 300 provides access for a guide wire 368, so that the guide wire can be threaded into the patient through the needle 365.

The medical professional using the device 300 can retract the needle by pressing a button 343, which disengages the needle retainer 342. The spring 360 then propels the needle 365 rearwardly so that the sharpened tip of the needle is enclosed within the shield 330. In this way, the contaminated needle 365 is protected against inadvertent contact.

As shown in FIG. 12, the barrel is a generally cylindrical barrel having a hollow central bore. A locking aperture 322 in the sidewall of the barrel 320 is configured to cooperate with the needle retainer 342 as described further below. The rearward end of the barrel is generally open for receiving the needle hub 340 and a connector hub 350. The forward end of the barrel 320 is generally closed, having a reduced diameter opening through which the needle 365 extends. Preferably, a seal 335, such as an O-ring forms a fluid seal between the reduced diameter opening and the needle 365 to prevent fluid from leaking from the shield 330 into the barrel 320 after retraction.

A pair of opposing axial slots 328 are formed in the interior surface of the barrel, adjacent the rearward end of the barrel. The slots 328 form a guide track that cooperates with the connector hub 350 to guide the needle 360 during retraction, as is discussed further below. Additionally, the slots 328 cooperate with the connector hub 350 to prevent the button 343 from being twisted relative to the locking aperture 322 when a fluid collection device is attached to the device 300 as is discussed further below. Although the barrel 320 may be formed as a single piece, in the present instance, the barrel is formed in two portions that are snap-fit together. Alternatively, the two portions can be connected by ultrasonic welding or adhesive.

The barrel 320 further includes a flange 327 projecting radially inwardly from the interior surface of the barrel, intermediate the length of the barrel. The flange 327 forms a stop that cooperates with the needle hub 340 to limit rearward displacement of the needle hub, which in turn limits the retraction of the needle. A keyway in the flange provides clearance for the button to pass through the flange 327 during retraction Referring again to FIGS. 12 and 13, the details of the needle hub 340 are illustrated. The needle hub 340 is generally cylindrical having an internal bore for receiving the needle 365. Preferably, the needle retainer 342 is integrally formed with the needle hub 340. The needle retainer includes an axially elongated radially deformable arm with a latch or button 343. The button 343 is configured to cooperate with the locking aperture 322 in the barrel, to releasably engage the needle hub 340 with the barrel 320. The forward end of the needle hub 340 flares outwardly forming a circumferential flange 345 having an external diameter corresponding to the central bore of the barrel. In this way, as the needle hub 340 is displaced rearwardly during retraction, the flange 345 slides along the interior bore to guide the needle hub.

The needle 365 is operable between a projecting position illustrated in FIG. 12 and a retracted position illustrated in FIG. 13. In the projecting position, the needle projects forwardly from the barrel so that the sharpened tip of the needle is exposed to pierce the patient and guide the shield 330 into the patient. In the retracted position, the sharpened tip of the needle is disposed within the shield 330 to prevent inadvertent contact with the contaminated needle. The spring 360 biases the needle 365 rearwardly toward the retracted position. The needle retainer 342 releasably retains the needle 365 in the projecting position against the bias of the spring 360.

The needle 365 extends through the central bore of the needle hub 340, and through the opening in the barrel tip 325 so that the sharpened tip of the needle projects forwardly from the barrel. The shield 330 is fixedly attached to the barrel tip 325 so that the shield also projects forwardly from the barrel 320. More specifically, the forward end of the barrel 320 forms a cavity or socket. A shield connector 332 is configured to cooperate with the cavity to fixedly attach the shield to the barrel. The shield connector 332 includes an internal bore approximately the same as the external diameter of the shield 330. The shield connector 332 forms an interference fit with the cavity on the barrel, which in turn provides an interference fit between the shield connector and the shield 330, thereby attaching the shield to the barrel. Alternatively, the shield 330 can be bonded to the shield connector 332. The depth in which the shield connector 332 is inserted into the cavity can be varied so that the length of the shield 330 overlapping the needle 365 can be varied. In this way the length of the needle 365 projecting forwardly from the shield can be controlled during manufacture.

The shield 330 is in the form of a relatively thin-walled cannula, overlying the needle 365 in telescoping relation. Specifically, the interior diameter of the shield is substantially the same as the external diameter of the needle 365. Preferably, the interior diameter of the shield 330 is the same as or several thousandths of an inch larger than the external diameter of the needle so that the needle 365 can readily slide within the shield.

Figure 14:
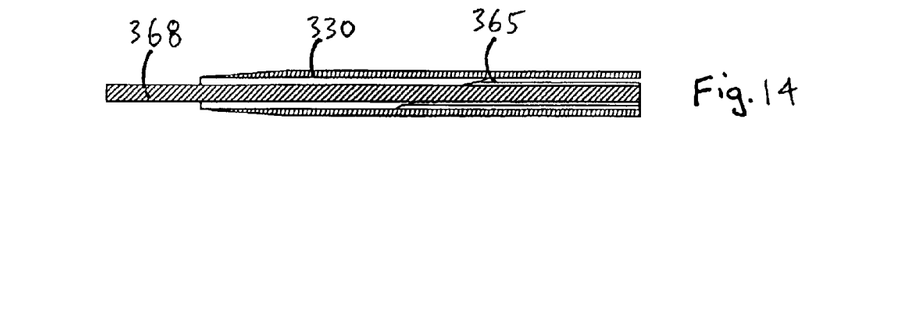
FIG. 14 is an enlarged fragmentary cross-sectional view of the portion designated A of the medical device illustrated in FIG. 13.

As shown in FIG. 14, the forward end of the shield 330 tapers inwardly forming a thin wall with a feather edge, which provides a smooth transition between the forward end of the shield 330 and the needle 365. In this way, when the needle 365 is inserted into the patient's vein or artery, the overlying shield 330 is also readily inserted into the patient's vein or artery.

A stop limits the rearward travel of the needle hub 340 to limit the distance that the needle 365 is retracted. Specifically, the forward end of the needle hub flares outwardly forming an enlarged head 345. The enlarged head 345 engages the flange 327 on the interior of the barrel 320 when the needle is retracted. In this way, the engagement between the flange 327 and the enlarged head 345 limits the rearward displacement of the needle 365.

Preferably, prior to retraction, the axial distance between the flange 327 and the enlarged head 345 is less than the length of the shield 330 that projects forwardly from the barrel 320. More specifically, preferably the axial distance is less than half the length of the shield that projects forwardly from the barrel 320. It is further preferable that the axial distance be substantially less than one quarter the length of the shield that projects from the barrel. In this way, after retraction, the sharpened tip of the needle is enclosed within the shield 330, rather than being retracted into the barrel 320.

The device 300 further includes elements for impeding re-extension of the needle 365 after retraction, so that the contaminated sharpened tip of the needle is not exposed. Specifically, as shown in FIG. 13, the forward end of the actuator button 343 forms a shoulder that engages the rearward shoulder of the flange 327 on the interior of the barrel. As the needle 365 is retracted, the needle retainer 342 flexes radially outwardly when it is displaced into the larger diameter of the rearward half of the barrel. The rearward edge of the forward half of the barrel forms a lip that operates as a stop engaging the button to prevent the needle from being displaced axially forwardly.

A connector hub 350 attached to the needle hub 340 provides an access port for inserting a guide wire 368 through the device 300 and into the patient. The connector hub 350 includes a central bore in fluid communication with the needle 365. In the present instance, the rearward end of the needle 365 is connected with the connector hub 350.

The connector hub 350 has an open rearward end and preferably forms a connector in the form of a Luer fitting for attaching a medical device, such as a syringe or guide wire feeder as discussed further below. In addition, preferably a lock 356 is formed on the rearward end of the connector hub for locking the separate device to the connector hub. More specifically, preferably, the lock 356 is a threaded Luer lock formed on the exterior of the connector hub.

In addition, a wire guide 352 is formed in the interior of the connector hub 350. The wire guide 352 is formed forward of the open end of the connector hub 350, and includes tapered walls, forming a generally frustoconical transition from the open end of the connector hub to a small diameter opening adjacent to and coaxial with the rearward end of the needle. The wire guide 352 operates similar to a funnel, guiding the wire into the small diameter opening of the needle as the wire is inserted through the large opening at the rearward end of the connector.

The connector hub 350 further includes a pair of opposing guide tabs 354 projecting radially outwardly into engagement with the guide tracks 328 formed in the interior of the barrel 320. The guide tabs 354 cooperate with the guide tracks 328 to guide the needle 365 rearwardly during retraction. In addition, the guide tabs 354 and guide tracks 328 operate as a circumferential lock preventing torque applied to the connector hub from being transferred to the needle retainer 342. In this way, if a fluid collection device, such as a syringe, is attached to the connector hub 350 by threading the syringe onto the connector hub, the torque applied to the connector hub is not transferred to the needle retainer 342, which could cause the needle retainer to break or disengage the locking aperture 322.

In the present instance, the needle hub 340 and connector hub 350 have been described as two separate elements connected together. However, the two elements can alternatively be formed as a single element.

Retracting the needle into the shield rather than the barrel has several benefits. The overall length of the barrel can be reduced because the barrel need not be long enough to accommodate the retracted needle. In addition, the needle 365 provides support for the shield 330 to prevent the shield from collapsing or buckling radially inwardly in response to external forces. For instance, the device 300 is used in conjunction with a guide wire. The guide wire is inserted vascularly into the patient through the needle 365. Prior to inserting the guide wire, and while the device 300 is inserted in the patient, the medical professional may actuate retraction by depressing the button 343. The needle retainer 342 is thereby displaced radially inwardly out of engagement with the barrel, and the spring 360 displaces the needle 365 rearwardly into the retracted position.

As shown in FIG. 13, the needle remains within the shield 330 after retraction. The shield 330 can then be inserted further into the patient without risk of piercing or coring the vein or artery. Depending on the material used for the shield and the wall thickness of the shield, the shield may not have sufficient columnar strength to overcome the resistance of inserting the length of the shield vascularly. In such instances, the needle provides additional rigidity so that the length of the shield can be inserted into the patient. After the length of the shield is inserted into the patient, the guide wire is threaded into the patient through the retracted needle and the shield.

After use, the shield 330 shields the sharpened tip of the needle 365 against inadvertent contact. Preferably, the shield 330 is somewhat flexible. In addition, the shield is preferably formed with sufficient column strength to prevent the shield 330 frown collapsing axially in response to an axial force after retraction. This columnar strength prevents the shield from readily buckling axially after retraction, which could expose the contaminated needle. In other words, the shield 330 is preferably laterally flexible, but is substantially axially incompressible. In the present instance the shield is formed of Teflon. However, a variety of other known plastic materials may be used to form the shield.

Configured in this way, the device 300 is preferably used to insert a guide wire as follows. The needle 365 and shield pierce the skin of a patient and the vein or artery of the patient. Upon inserting the needle vascularly, a flash of blood will flow through the device. The blood flash can be seen, indicating to the medical professional that a vein or artery has been pierced. A medical device, such as a syringe, is then attached to the connector hub 350 and an amount of blood is withdrawn from the patient to ensure that the needle is properly positioned within the patient's vein or artery. Alternatively, the syringe can be attached to the connector hub 350 prior to inserting the needle into the patient. If a syringe is used, the syringe plunger is withdrawn to form a vacuum that draws blood into the syringe barrel. Preferably, approximately 1–3 cc of blood are withdrawn to ensure that the needle is properly positioned.

After the blood is drawn, confirming that the needle 365 is properly positioned, the needle is retracted by depressing button 343. The spring then propels the needle 365 and needle hub 340 rearwardly so that the sharpened tip is shielded. The head 345 of the needle hub engages the flange 327 in the barrel 320 to stop the rearward displacement of the needle. The needle may be retracted so that the sharpened tip is disposed within the barrel. However, as discussed above, preferably, the needle tip is retracted into the shield 330. The shield and the shielded needle are then further inserted into the patient's vein or artery. Preferably, substantially the entire length of the shield is inserted into the patient.

After the shield 330 is inserted into the patient, the guide wire 368 is inserted into the patient. First, the syringe is detached from the connector hub 350. Blood may continue to flow through the connector hub 350 after the syringe is detached. The medical professional may control the flow of fluid by sealing the back end of the connector hub with his or her finger until he or she is ready to feed the guide wire. The guide wire 368 is then fed through the connector hub 350. The tapered surfaces of the wire guide 352 guides the guide wire 368 into the needle 365, so that feeding the wire through the connector hub 350 feeds the wire through the needle and shield 330, into the patient. Once the guide wire is inserted into the needle, the guide wire occludes most of the flow of blood through the device because the internal diameter of the needle is preferably substantially the same as the external diameter of the wire. After the guide wire is inserted into the patient, the device is withdrawn from the patient leaving the guide wire within the patient's vein or artery. Since the contaminated needle 365 is shielded, the device 300 can be safely disposed of without concern of an inadvertent needle stick.

Figure 15:
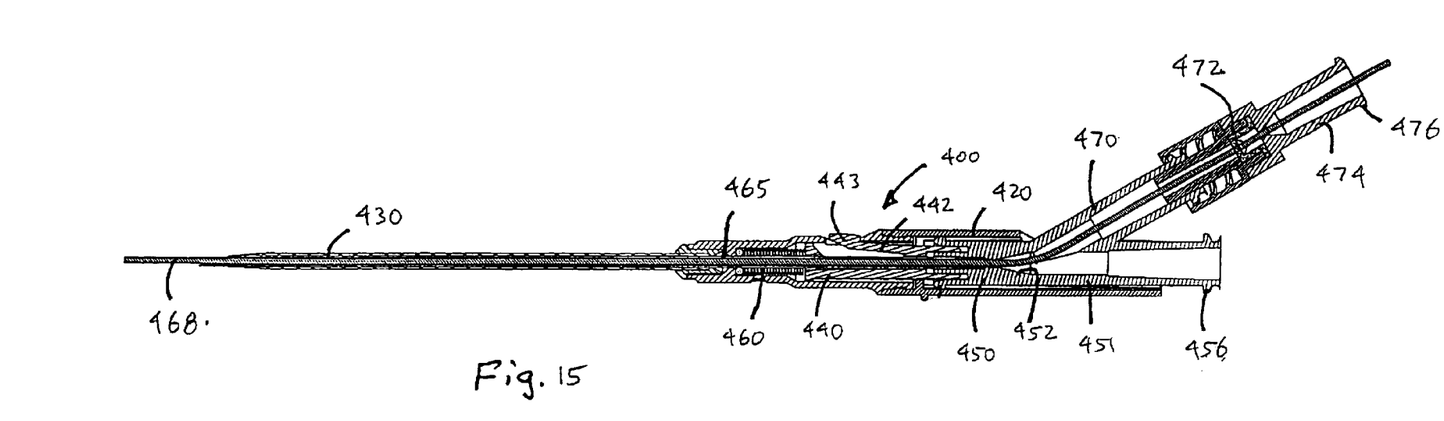
FIG. 15 is a cross-sectional view of an alternate embodiment of a medical device having a retractable needle for inserting a guide wire.
Figure 16:
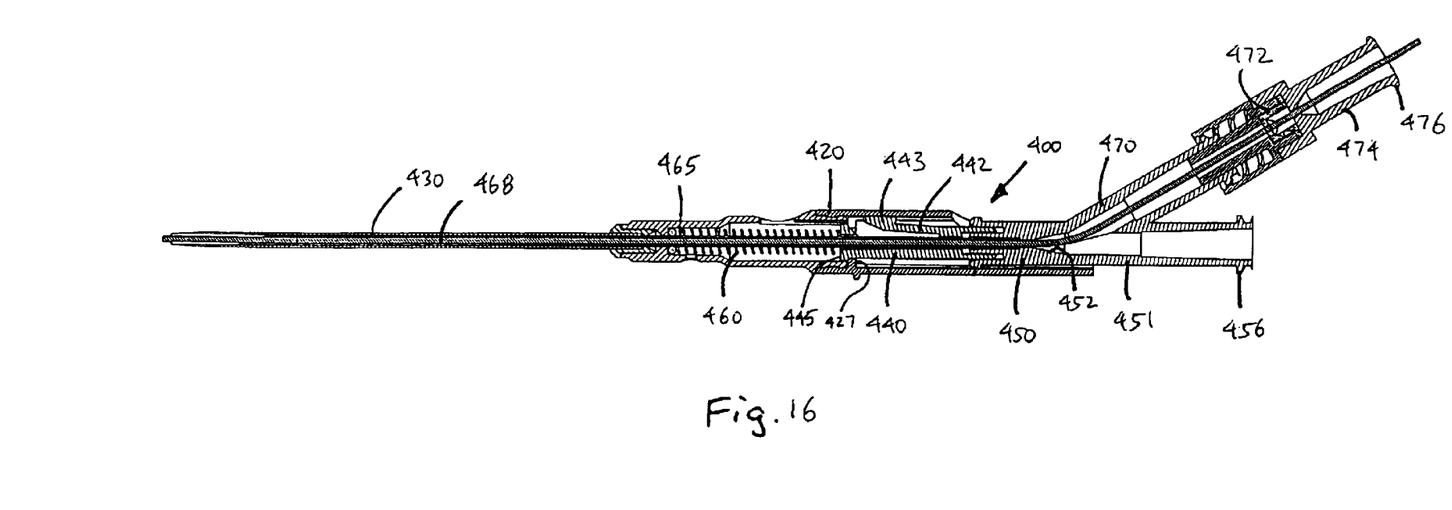
FIG. 16 is a cross-sectional view of the medical device illustrated in FIG. 15, illustrating the needle in a retracted position.

Referring now to FIGS. 15–16, a second embodiment of a guide wire insertion device is designated generally 400. The embodiment is similar to the embodiment 300, except that the second embodiment includes a Y-shaped connecting hub 450 having two ports. The two ports allow the device to virtually eliminate blood leakage, thereby providing a "bloodless" procedure as discussed in greater detail below.

The device 400 includes a retractable needle 465 for inserting a guide wire 468. The two ports of the connecting hub 450 allows the medical professional to attach a medical device, such as a syringe, to the first port to draw blood to ensure that the needle is properly placed in a vein, and then leave the syringe attached to the first port to prevent blood from leaking out the first port. The guide wire can then be inserted through the second port and into the patient. In this way, the device 400 substantially reduces or eliminates leakage of blood during the procedure.

Many of the elements of the device 400 are the same or similar to the elements of embodiment 300. For instance, the device 400 includes a barrel 420, a needle 465 projecting forwardly from the barrel, a needle shield 430 sheathing the needle, a spring 460 biasing the needle rearwardly, and a needle hub 440 having a needle retainer 442 releasably retaining the needle in the projecting position against the rearward bias of the spring.

However, the barrel 420 has a cut-out or slot for receiving the Y-shaped connector hub 450 having two ports rather than the single port of the connector hub 350. The connector hub 450 has a "straight through" portion or leg that is configured similarly to the rearward portion of the connector hub 350. The straight through portion 451 is axially aligned with the barrel 420 and the needle 465. The rearward end of the "straight through" leg 451 is generally open, and forms a connector, such as a Luer connector for attaching a separate medical device, such as a syringe, as described in connection with the first embodiment. A lock 456, such as a threaded Luer lock formed on the straight through leg 451 operates to lock the syringe onto the connector hub 450, sealing the rearward end of the straight through leg.

The second leg of the Y-connector hub 450 is referred to as the Y-leg or feeder leg 470. The feeder leg 470 is transverse the straight through leg 451, and is hollow. The feeder leg 470 can be configured similarly to the straight through leg 451 so that a syringe can be connected to the feeder leg rather than the straight through leg. However, preferably, the feeder leg 470 includes a hemostasis valve 472 that operates as a check valve preventing blood from leaking out the feeder leg, while allowing a guide wire 468 to be inserted into the device 400 through the feeder leg. A connector 474, such as a Luer hub having a Luer lock 476 is preferably connected to the feeder leg 470, rearward of the valve 472. The connector 474 allows a guide wire feeder 480, such as a hoop feeder to be attached to the device, as discussed further below.

In addition, a wire guide 452 is formed in the interior of the Y-connector hub 450. The wire guide may be formed to guide the wire from only one of the legs into the needle. However, preferably, the wire guide 452 is formed forward of the intersection of the enlarged bores of the straight through leg 451 and the feeder leg 470. The wire guide 452 is formed of tapered walls, forming a generally frustoconical transition from the large bores of the straight through leg 451 and the feeder leg 470 to a small diameter opening adjacent to and coaxial with the rearward end of the needle. The wire guide 452 operates similar to a funnel, guiding the wire into the small diameter opening as the wire is inserted into the large opening in either the feeder leg 470 or the straight through leg 451.

Configured in this way, the device 400 is operable to insert a guide wire 468 as follows. The needle 465 and shield 430 pierce the skin of a patient and the vein or artery of the patient. Upon inserting the needle vascularly, a flash of blood will flow through the device. A medical device, such as a syringe, is then attached to the connector hub 450 and an amount of blood is withdrawn from the patient to ensure that the needle is properly positioned within the patient's vein or artery. Alternatively, the syringe can be attached to the connector hub 450 prior to inserting the needle into the patient. If a syringe is used, the syringe plunger is withdrawn to form a vacuum that draws blood into the syringe barrel. Preferably, approximately 1–3 cc of blood is withdrawn to ensure that the needle is properly positioned.

After the blood is drawn confirming that the needle 465 is properly positioned, the needle is retracted by depressing button 443. The spring then propels the needle 465 and needle hub 440 rearwardly so that the sharpened tip is shielded. The head 445 of the needle hub engages the flange 427 in the barrel 420 to stop the rearward displacement of the needle. The needle may be retracted so that the sharpened tip is disposed within the barrel. However, as discussed above, preferably, the needle tip is retracted into the shield 430. The shield and the shielded needle are then further inserted into the patient's vein or artery. Preferably, substantially the entire length of the shield is inserted into the patient.

After the shield 430 is inserted into the patient, the guide wire 468 is inserted into the patient. The guide wire 468 is fed through the feeder leg 470. The tapered surfaces of the wire guide 452 guides the guide wire 468 into the needle 465, so that feeding the wire through the feeder leg 470 feeds the wire through the needle and shield 430, into the patient.

Since the guide wire 468 is not fed through the straight through leg 451, the syringe need not be removed from the Y-connector hub, so that the syringe seals the straight through leg, preventing blood from leaking out the straight through leg. In addition, the valve 472 attached to the feeder leg 470 prevents blood from leaking out the feeder leg as the guide wire is inserted into the patient. In this way, the device 400 is operable to achieve a "bloodless" method of inserting a guide wire into a patient, wherein little or no blood leaks from the device during use. In addition, after use, the sharpened tip of the needle 465 is shielded to prevent inadvertent needle sticks with the contaminated needle.

Figure 17:
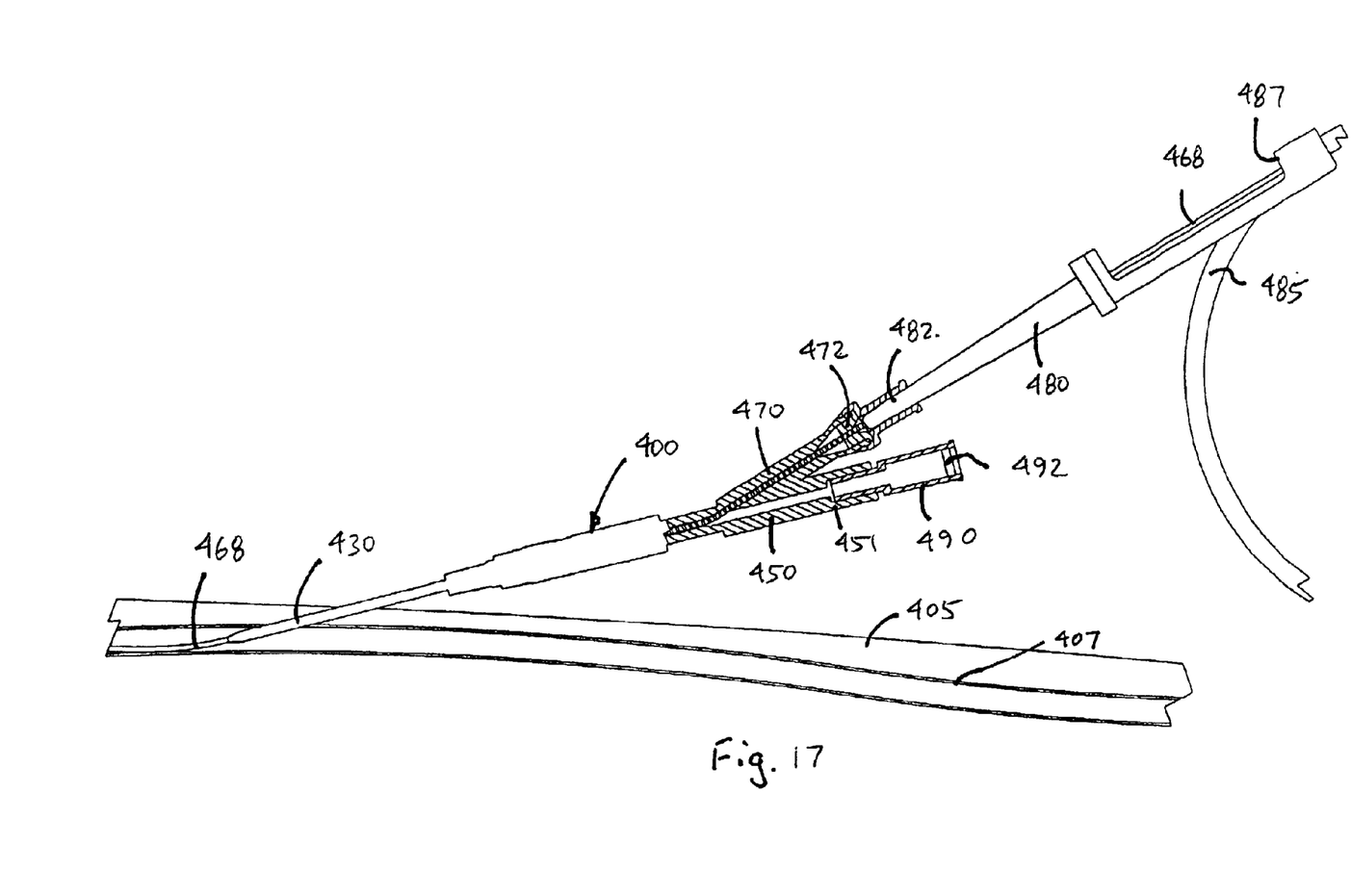
FIG. 17 is a side view partially in section of the medical device illustrated in FIG. 16 in combination with a guide wire feeder, illustrating the device inserted into a patient.
Figure 18:
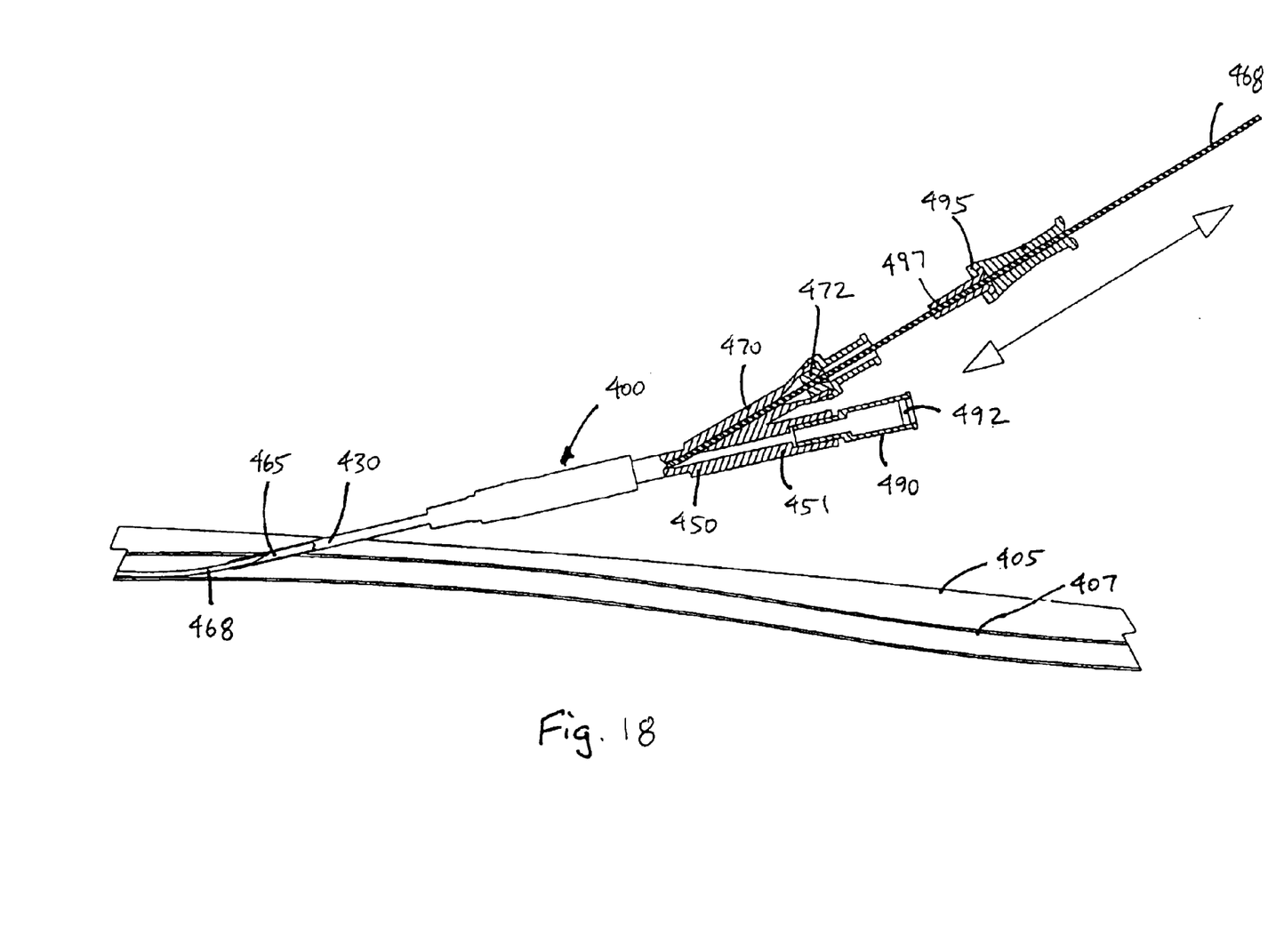
FIG. 18 is a side view partially in section of the medical device illustrated in FIG. 16 in combination with a guide wire gripper, illustrating the device inserted into a patient.

In FIGS. 17–18, the device 4000 is illustrated in use in a patient. In FIG. 17, the device 400 is illustrated in connection with a hoop feeder 480. The device is shown after vascular insertion, in which the needle 465 and shield 430 have pierced the patient's skin 405 and vein or artery 407. In FIG. 18 the shield 430 is shown partially broken away with the needle 465 retracted into the shield. In FIGS. 17 and 18, the guide wire 468 is shown being inserted into the patient with the shield 430 only partially advanced into the patient. However, preferably, substantially the entire length of the shield 430 is inserted into the patient prior to inserting the guide wire.

Referring again to FIG. 17, a hoop feeder 480 is shown. The hoop feeder includes a connector 482, such as a male Luer connector, that mates with the Luer connector 474 on the feeder leg 470 to attach the hoop feeder to the device 400. The hoop feeder 480 also includes a length of guide wire 468 sheathed by one or more convolutions of a casing, such as a plastic casing 485. A cut-out or window 487 in the casing 485 provides access to the guide wire 468. The medical professional engages the guide wire 468 in the window 487 to advance the guide wire into the patient through the device.

In FIG. 17, the device 400 is also shown in connection with a dead-end connector 490 attached to the rearward end of the straight through leg 451. Such a dead-end connector can also be attached to the connector hub 350 of the previous embodiment. The dead-end connector 490 seals the straight through leg 451 to prevent blood from leaking out the straight through leg. The dead-end connector can be attached to the straight through leg after blood is drawn into a syringe. For such use, the syringe is detached after the blood is drawn, and the dead-end connector is attached in place of the syringe.

Alternatively, and preferably, the dead-end connector 490 includes a hollow interior forming a reservoir for receiving blood. A vent plug 492 in the form of a hydrophobic filter prevents blood from leaking out the back end of the dead-end connector, while allowing air to flow through to prevent the connector from becoming line locked, so that blood can flow into the connector. Preferably the connector 490 is transparent or translucent so that the medical professional can see the blood flowing into the connector.

The dead-end connector 490 can be used in one of several ways. First, the connector 490 can operate as a flash-back chamber. In this manner, the dead-end connector 490 is attached to the straight through leg 451 prior to piercing the patient with the needle 465. After the medical professional pierces the patient with the needle and sees a flash of blood in the connector, the connector is removed and a syringe or similar device is attached to the straight through leg 451 to draw blood to ensure that the needle 465 is properly positioned.

Alternatively, the dead-end connector 490 can operate as the indicator that the needle is properly positioned within the patient's vein or artery. In this manner, if blood flows adequately into the dead-end connector 490, the medical professional retracts the needle and then inserts the shield further into the patient. Since the connector 490 operates as the blood flow indicator, a syringe need not be attached, and the dead-end connector 490 remains attached to the straight through leg 451 to seal it against blood leakage.

Referring again to FIG. 18, the device 400 is illustrated without a feeder, such as the hoop feeder 480 illustrated in FIG. 17. In such use, the medical professional inserts the guide wire 468 by grasping the wire and feeding the wire into the feeder leg. Preferably the medical professional uses a tool to grasp the wire. In one manner, the medical professional grasps the wire with tweezers, advancing the wire with the tweezers, then releasing the wire and re-grasping the wire rearward to advance more of the guidewire.

FIG. 18 also illustrates an alternative and preferred tool 495 for grasping the guide wire to feed the guide wire. The gripping tool 495 is formed of a plastic material, and is preferably formed of an elastomeric material so the it is resilient. The gripping tool comprises a pair of jaws 497 for gripping the wire, and a through-bore for receiving the guide wire 468. The through bore is sized slightly larger than the wire diameter so that the wire can readily pass through the gripper 495.

By grasping the sides of the gripper 495, the gripper clamps onto the guide wire 468 so that the medical professional can advance the wire into the patient. After advancing the guidewire 468, the medical professional releases his or her grip of the gripper, which releases the gripper jaws 497 from clamping onto the wire. The medical professional then slides the gripper rearwardly along the wire, then squeezes the gripper to grasp the wire to advance the wire further into the patient. Additionally, preferably the forward portion of the gripper forms a nose configured to cooperate with the open end of the feeder port 470.

The terms and expressions which have been employed are used as terms of description and not of limitation. There is no intention in use of such terms and expressions of excluding any equivalents of the features shown and described or portions thereof. It is recognized, however that various modifications are possible within the scope and spirit of the invention as set forth in the following claims.

What is claimed is:

1. A medical device, comprising:

a hollow housing;

a needle having a sharpened tip projecting forwardly from the housing;

a biasing element biasing the needle rearwardly;

a needle retainer releasably retaining the needle against the rearward bias of the biasing element;

a flexible shield fixedly attached to the housing, projecting forwardly from the housing;

the shield having a forward edge and being configured for insertion into a patient;

the shield sheathing the needle such that in a projecting position, the sharpened tip of the needle projects beyond the forward edge of the shield, and in a retracted position the sharpened tip is enclosed within the shield;

wherein upon actuation of the needle retainer, the biasing element displaces the needle rearwardly so that the sharpened tip of the needle is enclosed within the shield, wherein the shield is substantially puncture resistant wherein the axial force required to buckle the shield is less than the force necessary to puncture the shield with the needle to prevent inadvertent contact with the contaminated needle.

2. The medical device of claim 1 comprising a lock for locking the needle in the retracted position to substantially permanently retain the needle against being re-extended into the projecting position.

3. The medical device of claim 1 wherein the biasing element is a spring.

4. The medical device of claim 1 comprising a connector in fluid communication with the needle for attaching a fluid device for fluid transfusion through the needle.

5. The medical device of claim 1 comprising a stop operable to limit the rearward displacement of the needle, wherein the stop is positioned such that the displacement of the needle from the projecting position to the retracted position is less than the length of the shield.

6. A medical device, comprising:

a hollow housing;

a needle having a sharpened tip projecting forwardly from the housing;

a biasing element biasing the needle rearwardly;

a needle retainer releasably retaining the needle against the rearward bias of the biasing element;

a shield fixedly attached to the housing, projecting forwardly from the housing;

the shield being configured for insertion into a patient;

the shield sheathing the needle such that in the projecting position, the sharpened tip of the needle projects beyond the forward edge of the shield, and in the retracted position the sharpened tip is enclosed within the shield;

wherein upon actuation of the needle retainer, the biasing element displaces the needle rearwardly so that the sharpened tip of the needle is enclosed within the shield, wherein the shield is substantially puncture resistant wherein the axial force required to buckle the shield is less than the force necessary to puncture the shield with the needle to prevent inadvertent contact with the contaminated needle.

7. The medical device of claim 6 comprising a lock for locking the needle in the retracted position to substantially permanently retain the needle against being re-extended into the projecting position.

8. The medical device of claim 6 wherein the biasing element is a spring.

9. The medical device of claim 6 comprising a connector in fluid communication with the needle for attaching a fluid device for fluid transfusion through the needle.

10. The medical device of claim 6 comprising a stop operable to limit the rearward displacement of the needle, wherein the stop is positioned such that the displacement of the needle from the projecting position to the retracted position is less than the length of the shield.

* * * * *